United States Patent
Helton et al.

(10) Patent No.: US 10,398,687 B2
(45) Date of Patent: Sep. 3, 2019

(54) USE OF CYPROHEPTADINE TO TREAT ORGANOPHOSPHATE EXPOSURE

(76) Inventors: David Reed Helton, Dana Point, CA (US); David Brian Fick, Coto de Caza, CA (US)

( * ) Notice: Subject to any disclaimer, the term of this patent is extended or adjusted under 35 U.S.C. 154(b) by 163 days.

(21) Appl. No.: 13/232,917

(22) Filed: Sep. 14, 2011

(65) Prior Publication Data
US 2012/0065194 A1     Mar. 15, 2012

Related U.S. Application Data

(60) Provisional application No. 61/382,900, filed on Sep. 14, 2010.

(51) Int. Cl.
| | |
|---|---|
| *A61K 31/451* | (2006.01) |
| *A61K 31/46* | (2006.01) |
| *A61K 31/5513* | (2006.01) |

(52) U.S. Cl.
CPC ............ *A61K 31/451* (2013.01); *A61K 31/46* (2013.01); *A61K 31/5513* (2013.01)

(58) Field of Classification Search
CPC ... A61K 31/451; A61K 31/46; A61K 31/5513
See application file for complete search history.

(56) References Cited

U.S. PATENT DOCUMENTS

| | | |
|---|---|---|
| 3,014,911 A | 12/1961 | Engelhardt et al. |
| 3,851,059 A | 11/1974 | Prugh et al. |

OTHER PUBLICATIONS

Sarkar et al. (Behavioural Brain Research 109, 2000, 187-193).*
Lee (JAMA, Aug. 6, 2003, 290, 5, 659-661).*
Volans (J Accid Emerg Med 1996, 13, 202-206).*
Zesiewicz et al. (Movement Disorders, 17, 6, 2002, p. 1365-67).*

\* cited by examiner

*Primary Examiner* — Umamaheswari Ramachandran
(74) *Attorney, Agent, or Firm* — Loza & Loza, LLP; Michael F. Fedrick

(57) ABSTRACT

A method of treating exposure to an organophosphate compound by administering a cyproheptadine compound to a subject in need thereof.

11 Claims, No Drawings

USE OF CYPROHEPTADINE TO TREAT ORGANOPHOSPHATE EXPOSURE

BACKGROUND

Organophosphate compounds, in particular organic esters of substituted phosphoric acids, have been developed for use as chemical weapons. These compounds inhibit cholinesterases and disrupt the peripheral nervous system by preventing these enzymes from breaking down acetylcholine. Some organophosphate compounds are sufficiently potent that even brief exposure may be fatal.

Organophosphate anticholinesterase agents include tabun (Ethyl N,N-dimethylphosphoramidocyanidate, also referred to as GA), sarin (O-Isopropyl methylphosphonofluoridate, also referred to as GB), soman (O-Pinacolyl methylphosphonofluoridate, also referred to as GD), and VX (O-ethyl-S-[2(diisopropylamino)ethyl]methylphosphonothiolate). Tabun, sarin, and soman in particular are highly volatile and easily disseminated in vapor form. They are also readily absorbed through the lungs, eyes, skin, and intestinal tract.

Individuals who survive exposure to organophosphate nerve agents may experience morbidity as a result of such exposure. Some survivors of sarin exposure, for example, have exhibited conditions including post traumatic stress syndrome, memory deficits and altered evoked potentials (Murata K, Araki S, Yokoyama K, Okumura T, Ishimatsu S, Takasu N and White R F, Asymptomatic sequelae to acute sarin poisoning in the central and autonomic nervous system 6 months after the Tokyo subway attack, *J Neurol* 244: 601-606, 1997). Munitions workers exposed to organophosphate agents in the U.S. demonstrated EEG changes, while a similar population in Russia showed long lasting memory loss, sleep disorders and neurological impairments (Romano J A, McDonough J H Jr, Sheridan R E and Sidell F R. "Health Effects of Low-Level Exposure to Nerve Agents," *Chemical Warfare Agents: Toxicity at Low Levels*, edited by Somani S M and Romano J A, CRC Press, 2001, pp. 1-24; Duffy F H, Burchfiel J L, Bartels P H, Gaon M and Sim V M, "Long-Term Effects of An Organophosphate Upon the Human Encephalogram," *Toxicology and Applied Pharmacology*, 1979, 47: 161-176).

No effective therapies currently exist for treating the long-term effects of exposure to organophosphate agents in individuals who survive such exposure. In addition, the current standard of care for treating acute organophosphate exposure, namely the injection of atropine, carries a risk of adverse reactions. In view of the threat posed by organophosphate agents, improved therapies for treating individuals exposed to such agents and for preventing the harm that these agents can cause are needed.

SUMMARY

Cyproheptadine is an antihistamine and is typically used in the treatment of the symptoms associated with allergies. It is also known to be an antiserotonergic agent, and has been used for a number of other conditions, such as serotonin syndrome (drug induced excess of intrasynaptic 5-hydroxytryptamine), as well as having anticholinergic properties. Cyproheptadine has not heretofore been used to treat exposure to organophosphate compounds, in particular organophosphate nerve agents. The present method of treating exposure to organophosphate agents with cyproheptadine and derivatives thereof therefore represents a new tool for treating both military and civilian personnel exposed to a nerve agent attack.

The present method is a treatment for exposure to an organophosphate compound, namely by the administration to a subject in need thereof a therapeutically effective amount of a pharmaceutical composition comprising one of the following formulas:

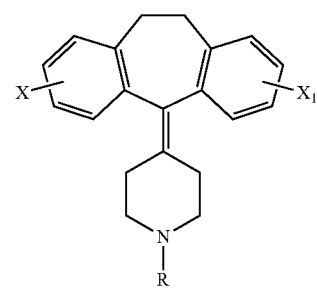

In these compounds, and pharmaceutically acceptable salts and esters thereof, X and $X_1$ can be different or the same, and:
  (a) X can be selected from the group consisting of hydrogen, a halo group, a C1-4 alkyl group, a C1-4 alkoxy group, and an aryl group;
  (b) $X_1$ can be selected from the group consisting of hydrogen, a halo group, a C1-4 alkyl group, a C1-4 alkoxy group, and an aryl group; and
  (c) R can be selected from the group consisting of hydrogen, a C1-4 alkyl group, and a C1-4 alkenyl group.

The C1-4 alkyl group of X and/dr $X_1$ can be a halogen substituent or trifluoromethyl group, and the aryl group can be a substituent selected from the group consisting of a halo group, a C1-4 alkyl group, and a C1-4 alkoxy group. The C1-4 alkyl group and the C1-4 alkenyl group or R can comprise a substituent selected from the group consisting of a hydroxy group, a mesyloxy group or an amino group. In addition, one or more of the 2, 3, 5, and 6 positions of the piperidine ring of the foregoing compound can be substituted with C1-4 alkyl groups. Preferably, the compound is cyproheptadine, and is formulated with a pharmaceutically acceptable excipient.

The compound is preferably administered in a therapeutically effective dose of between 0.1 and 10 mg/kg, and preferably about 3 mg/kg. The compound can be administered to a subject either prior to or following exposure of the subject to an organophosphate compound. The present composition can further be administered alone, or can be administered together with atropine. Alternatively, the compound can replace atropine in a treatment regimen further comprising the administration of pralidoxime (2-PAM) and/or diazepam. The foregoing treatments can be administered in order to treat exposure to sarin, tabun, soman, VX or an organophosphate insecticide.

DESCRIPTION

It has been discovered that cyproheptadine compounds can be effectively used as a chemical warfare agent (CWA) countermeasure, as a supplement to or a replacement for atropine, which is the current standard antidote for exposure to organophosphate agents. Cyproheptadine has been found to be effective as both a pre-treatment and post-treatment when given alone against organophosphate agents such as sarin, and can in fact replace atropine with equivalent efficacy in promoting survival following organophosphate exposure. While effective doses of atropine can produce debilitating side effects, cyproheptadine is safe and well tolerated, and has been shown to be neuroprotective. Cyproheptadine can thus be used both as a treatment for CWA exposure and as an agent to reduce or eliminate the side effects of anti-cholinergics such as atropine.

Treatments for exposure to organophosphate chemical warfare agents typically rely on a combination of agents that increase the chances of survival and block the cholinergic response to CWAs. Current therapies for protecting the central nervous system (CNS) from the long term neurodegeneration produced by CWA exposure are time and dose dependent, and would benefit from the addition of another potent CNS protective agent, such as cyproheptadine. When added to lower doses of atropine, cyproheptadine produced greater survival than did the standard atropine dose.

Definitions

As used herein, the following terms and variations thereof have the meanings given below, unless a different meaning is clearly intended by the context in which such term is used.

"Alkyl" refers to saturated aliphatic groups including straight-chain, branched-chain, and cyclic groups, all of which can be optionally substituted. Preferred alkyl groups contain 1 to 10 carbon atoms. Suitable alkyl groups include methyl, ethyl, and the like, and can be optionally substituted. The term "heteroalkyl" refers to carbon-containing straight-chained, branch-chained and cyclic alkyl groups, all of which can be optionally substituted, containing at least one O, N or S heteroatom. The term "alkoxy" refers to the ether —O-alkyl, where alkyl is defined as above.

"Alkenyl" refers to unsaturated groups which contain at least one carbon-carbon double bond and includes straight-chain, branched-chain, and cyclic groups, all of which can be optionally substituted. Preferable alkenyl groups have 2 to 10 carbon atoms. The term "heteroalkenyl" refers to unsaturated alkenyl groups which contain at least one carbon-carbon double bond and includes straight-chained, branch-chained and cyclic groups, all of which can be optionally substituted, containing at least one O, N or S heteroatom.

"Aryl" refers to aromatic groups that have at least one ring having a conjugated, pi-electron system and includes carbocyclic aryl and biaryl groups, both of which can be optionally substituted, as well as aralkyl, aralkenyl, and heteroaryl groups. The term "aralkyl" refers to an alkyl group substituted with an aryl group. Suitable aralkyl groups include benzyl and the like; these groups can be optionally substituted. The term "aralkenyl" refers to an alkenyl group substituted with an aryl group. The term "heteroaryl" refers to carbon-containing 5-14 membered cyclic unsaturated radicals containing one, two, three, or four O, N, or S heteroatoms and having 6, 10, or 14 $\pi$-electrons delocalized in one or more rings, e.g., pyridine, oxazole, indole, thiazole, isoxazole, pyrazole, pyrrole, each of which can be optionally substituted as discussed above. Preferred aryl groups have 6 to 10 carbon atoms.

"Derivative" refers to a compound that has been chemically modified or partially substituted with another chemical or chemical group, as compared to a reference starting compound.

"Halo" refers to chlorine, bromine, fluorine, or iodine.

"Organophosphate compound" refers to an ester of phosphoric acid which acts on the enzyme acetylcholinesterase and have neurotoxicity. Organophosphate compounds include nerve agents such as tabun (Ethyl N,N-dimethylphosphoramidocyanidate, also referred to as GA), sarin (O-Isopropyl methylphosphonofluoridate, also referred to as GB), soman (O-Pinacolyl methylphosphonofluoridate, also referred to as GD), and VX (O-ethyl-S-[2(diisopropylamino)ethyl]methylphosphonothiolate), as well as some compounds used as insecticides, such as phosphoric acid diethyl 4-nitrophenyl ester (paraoxon), diethyl-p-nitrophenyl monothiophosphate (parathion) and phosphorothioic acid O-(3-chloro-4-methyl-2-oxo-2H-1-benzopyran-7-yl) O,O-diethyl ester (coumaphos).

A "subject" refers a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

"Treat" and "treatment," with respect to the exposure of a subject to an organophosphate compound, refer to a medical intervention which attenuates, prevents, and/or counteracts the effects of such exposure. The foregoing terms can refer to the prophylactic administration of the present compounds and compositions to subjects at risk of exposure to an organophosphate compound prior to an anticipated exposure, and/or can refer to the administration of the present compounds and compositions following such exposure.

As used herein, the term "comprise" and variations of the term, such as "comprising" and "comprises," are not intended to exclude other additives, components, integers or steps. The terms "a," "an," and "the" and similar referents used herein are to be construed to cover both the singular and the plural unless their usage in context indicates otherwise.

Compounds

The compounds used in the present method comprise cyproheptadine and derivatives of cyproheptadine, in particular those cyproheptadine compounds represented by the following formula:

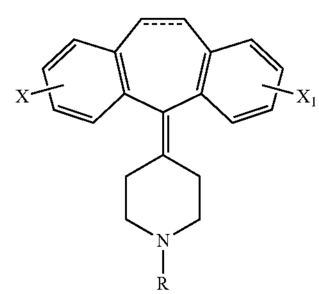

wherein which R is hydrogen or lower alkyl or alkenyl containing between 1 and 4 carbon atoms and which may be straight or branched chained. The alkyl radical may be substituted, for example, with a hydroxy, a mesyloxy or an amino group. The presence of either a single bond or a double bond between the 10 and 11 carbon atoms is indicated by the dotted line.

The X and $X_1$ substituents may be hydrogen or a halogen, for example chlorine, bromine or fluorine, but X and $X_1$ also may be radicals such as trifluoromethyl, lower alkyl having up to four carbon atoms, lower alkoxy having up to four carbon atoms, or a aryl radical such as phenyl. The X and $X_1$ substituents may be similar or may be dissimilar and each benzene ring may have one or two of the aforementioned substituents attached to it. One or more of the hydrogens in positions 2, 3, 5, and 6 of the piperidine ring may be replaced by alkyl groups, although the total number of carbon atoms in all such substituent alkyl groups does not exceed four.

In a preferred embodiment, the compound used in the present methods is cyproheptadine (also referred to as cycloheptadine, IUPAC name 4-(5H-dibenzo [a,d]cyclohepten-5-ylidene)-1-methylpiperidine hydrochloride), represented by the following formula:

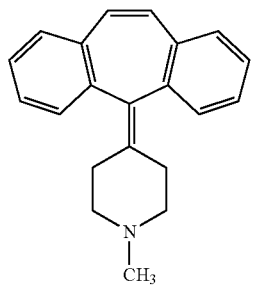 [SMILES: CN1CCC(=C2c3ccccc3C=Cc3ccccc32)CC1]

Synthesis of cyproheptadine and derivatives thereof is known to the art, for example in U.S. Pat. Nos. 3,014,911 and 3,851,059. The present compounds can be prepared, for example, from appropriately substituted 5H-dibenzo[a,d] cycloheptenones. For example, a 5H-dibenzo[a,d]cyclohepten-5-one or a derivative containing an X and/or X' substituent in the benzene rings is treated with a Grignard reagent prepared from a 1-alkyl-4-halo-piperidine or a ring alkylated 1-alkyl-4-halo-piperidine to form an intermediate carbinol, a 5-hydroxy-5-(1-alkyl-4-piperidyl)-5H-dibenzo [a,d]cycloheptene which is then dehydrated to produce the desired starting material, a 1-alkyl-4-(5H-dibenzo[a,d]cyclohepten-5-ylidene)piperidine. The starting material employed, preferably in the form of its hydrobromide salt, is then treated with bromine to produce the corresponding 10,11-dibromo-10,11 dihydro-dibenzo-cycloheptene, preferably isolated as the hydrobromide, and subsequently the dibromo compound is treated with a strong base to form a mono-bromo 5H-dibenzo[a,d]cycloheptene compound which mono-bromo compound is then contacted with a piperidine or pyrrolidine in the presence of a strong base to produce a 10-enamine derivative. The resulting 10-enamine derivative is then hydrolyzed to produce a biologically active 10-keto compound which is readily reduced to the corresponding 10-hydroxy compound which also is a pharmacologically active compound of the present invention.

Pharmaceutical Compositions

A pharmaceutical composition can comprise one or more of the present compounds. Such a composition preferably comprises: (1) a therapeutically effective amount of one or more of the present compounds (and/or salts and esters thereof); and (2) a pharmaceutically acceptable excipient.

A pharmaceutically acceptable excipient, including carriers, can be chosen from those generally known in the art including, but not limited to, inert solid diluents, aqueous solutions, or non-toxic organic solvents, depending on the route of administration. If desired, these pharmaceutical formulations can also contain preservatives and stabilizing agents and the like, for example substances such as, but not limited to, pharmaceutically acceptable excipients selected from the group consisting of wetting or emulsifying agents, pH buffering agents, human serum albumin, antioxidants, preservatives, bacteriostatic agents, dextrose, sucrose, trehalose, maltose, lecithin, glycine, sorbic acid, propylene glycol, polyethylene glycol, protamine sulfate, sodium chloride, or potassium chloride, mineral oil, vegetable oils and combinations thereof. Those skilled in the art will appreciate that other carriers also can be used.

Liquid compositions can also contain liquid phase excipients either in addition to or to the exclusion of water. Examples of such additional liquid phases are glycerin, vegetable oils such as cottonseed oil, organic esters such as ethyl oleate, and water-oil emulsions.

Formulations suitable for parenteral administration, such as, for example, by intravenous, intramuscular, intradermal, and subcutaneous routes, include aqueous and non-aqueous isotonic sterile injection solutions. These can contain antioxidants, buffers, preservatives, bacteriostatic agents, and solutes that render the formulation isotonic with the blood of the particular recipient. Alternatively; these formulations can be aqueous or non-aqueous sterile suspensions that can include suspending agents, thickening agents, solubilizers, stabilizers, and preservatives. In a further alternative, the present compositions can formulated as aerosols or other inhalable formulations. The pharmaceutical compositions of the present invention can be formulated for administration by any of a number of routes, including intravenous infusion, oral, topical, intraperitoneal, intravesical, transdermal, intranasal, rectal, vaginal, intramuscular, intradermal, subcutaneous and intrathecal routes.

Preclinical Models and Clinical Evaluation

In order to screen for the most effective of the present compounds and pharmaceutical compositions and determine appropriate candidates for further development, as well as to determine appropriate dosages of such compounds and compositions for a human subject, preclinical animal models can be used. Exemplary animal models are set forth below. Preferably, a series of tests is performed in animal models to screen for activity in treating and/or preventing the effects of exposure to nerve agents.

Compounds and compositions are preferably selected using a panel of pre-clinical tests. Preliminary screening tests can be used to determine appropriate dosages to test in follow-on models. Appropriately selected doses of compounds and compositions tested in this way can then be subjected to testing for efficacy against nerve agent exposure.

A. Evaluation of Prophylactic Protection from Nerve Agent Exposure

Male ICR mice from Charles River (20 to 30 grams average weight) are treated with one of the present compounds i.m. 15 or 60 minutes, or by gavage 30 or 120 minutes, before challenge with a dose of 2×LD50 of soman (LD50=98 µg/kg without atropine, LD50=130 µg/kg with 11.2 mg/kg of atropine). As a negative control, saline is administered instead of a test compound. As a positive control for survival, pyridostigmine (0.1 mg/kg, i.m. or 0.82 mg/kg orally) is administered to a separate group of animals.

All subject animals receive atropine sulfate (11.2 mg/kg) and 2-PAM (25 mg/kg) i.m. exactly 10 seconds after soman challenge, using a total dose volume of 0.5 ml/kg body weight. All animals are then allocated to pretreatment cells in a randomized block design. Groups of ten mice are used in each experiment and survivors in each group are noted after 24 hours. The 24-hour survival of animals pretreated with each dose of one of the present compounds is compared with the 24-hour survival observed in the negative control group. A survival difference of at least four indicates improved efficacy of the candidate compound over that observed with the negative control group.

Once improved efficacy of a candidate compound is shown, the candidate can further be tested for efficacy in the absence of atropine and/or 2-PAM administration. This can lead to the identification of compounds capable of providing at least partial prophylaxis with respect to the effects of organophosphate nerve agent exposure when used as single agents.

In vitro models of neuroprotection can also be used to evaluate candidate compounds. Nerve Growth Factor (NGF) and its cell surface target play a role in neuronal cell differentiation, growth and repair mechanisms and offers neuroprotection in in vitro experiments. The present compounds can be tested as a cytoprotective agent in neuronal cells deprived of growth factor (NGF and serum) for 24 hours.

B. Evaluation of Post-Exposure Protection from Nerve Agents

Male ICR mice from Charles River (20 to 30 grams average weight) are treated with one of the present compounds administered i.m. 10 seconds after challenge with a dose of 2×LD50 of soman or tabun (aqueous solution containing 0.9% NaCl). Compounds are given simultaneously with atropine sulfate (11.2 mg/kg). As a negative control, atropine sulfate (11.2 mg/kg) and 2-PAM (25 mg/kg) are given without a test compound (no mice would be expected to survive). As a positive control for survival, HI-6 (9.6 mg/kg) is administered with atropine sulfate (11.2 mg/kg) to a separate group of animals. All injections are administered i.m. using a dose volume of 0.5 mL/kg body weight.

All animals are allocated to treatment cells in a randomized block design. Groups of ten mice are used in each experiment and survivors in each group are noted after 24 hours. The 24-hour survival of animals injected with each dose of a test compound is compared to the 24-hour survival observed in the negative control group. A survival difference of at least four indicates improved efficacy of the candidate compound over that observed with the negative control group.

C. Clinical Development

Following the testing of candidate compounds and/or compositions in preclinical animal models, candidates for further development can be selected based on the criteria set forth above. One or more selected candidates having desirable preclinical profiles can then be subjected to clinical evaluation in human subjects using methods known to those of skill in the art.

Treatment Methods

The effects of nerve agent exposure can be prevented or ameliorated by administering therapeutically effective amounts of one or more of the present compounds and/or pharmaceutical compositions to a patient in need thereof. The present compounds and/or compositions are administered to a patient in a quantity sufficient to treat or prevent the symptoms and/or the underlying etiology associated with nerve agent exposure in the patient. The present compounds can also be administered in combination with other agents known to be useful in the treatment of nerve agent exposure, such as atropine sulfate, diazepam, and pralidoxime (2-PAM), either in physical combination or in combined therapy through the administration of the present compounds and agents in succession (in any order).

Administration of the present compounds and compositions can begin immediately following exposure to an organophosphate nerve agent, preferably within the first hour following exposure, and more preferably within one to five minutes. Administration of the compositions and compounds can alternatively begin prior to an anticipated exposure (such as impending combat), in order to prevent or reduce the impact of subsequent exposure. Prophylactic treatment with the present compositions preferably occurs within the half life of the compound in vivo, and in any event within the time period during which the compound remains effective. The present invention thus includes the use of the present compounds and/or a pharmaceutical composition comprising such compounds to prevent and/or treat exposure to a nerve agent.

Depending upon the particular needs of the individual subject involved, the present compounds can be administered in various doses to provide effective treatments for nerve agent exposure. Factors such as the activity of the selected compound, half life of the compound, the physiological characteristics of the subject, the extent or nature of the subject's exposure or condition, and the method of administration will determine what constitutes an effective amount of the selected compounds. Generally, initial doses will be modified to determine the optimum dosage for treatment of the particular subject. The compounds can be administered using a number of different routes including oral administration, topical administration, transdermal administration, intraperitoneal injection, or intravenous injection directly into the bloodstream. Effective amounts of the compounds can also be administered through injection into the cerebrospinal fluid or infusion directly into the brain, if desired. In view of the long-term effects of low-dose exposure to nerve agents, it is contemplated that repeated doses of the present compounds administered over an extended period of time may be required.

An effective amount of any embodiment of the present invention is determined using methods known to pharmacologists and clinicians having ordinary skill in the art. For example, the animal models described herein can be used to determine applicable dosages for a patient. As known to those of skill in the art, a very low dose of a compound, i.e. one found to be minimally toxic in animals (e.g., 1/10×LD10 in mice), can first be administered to a patient, and if that dose is found to be safe, the patient can be treated at a higher dose. A therapeutically effective amount of one of the present compounds for treating nerve agent exposure can then be determined by administering increasing amounts of such compound to a patient suffering from such exposure until such time as the patient's symptoms are observed or are reported by the patient to be diminished or eliminated.

In a preferred embodiment, the present compounds and compositions selected for use in treating or preventing nerve agent exposure have a therapeutic index of approximately 2 or greater. The therapeutic index is determined by dividing the dose at which adverse side effects occur by the dose at which efficacy for the condition is determined. A therapeutic index is preferably determined through the testing of a number of subjects. Another measure of therapeutic index is the lethal dose of a drug for 50% of a population ($LD_{50}$, in a pre-clinical model) divided by the minimum effective dose for 50% of the population ($ED_{50}$).

Blood levels of the present compounds can be determined using routine biological and chemical assays and these blood levels can be matched to the route of administration and half life of a selected compound. The blood level and route of administration can then be used to establish a therapeutically effective amount of a pharmaceutical composition comprising one of the present compounds for preventing and/or treating nerve agent exposure.

Exemplary dosages in accordance with the teachings of the present invention for these compounds range from 0.0001 mg/kg to 60 mg/kg, though alternative dosages are contemplated as being within the scope of the present invention. Preferably, dosages of 0.1 mg/kg, 0.5 mg/kg, 1 mg/kg, 3 mg/kg, 5 mg/kg, 10 mg/kg, 20 mg/kg or higher are administered. Suitable dosages can be chosen by the treating physician by taking into account such factors as the size, weight, age, and sex of the patient, the physiological state of the patient, the severity of the condition for which the compound is being administered, the response to treatment, the type and quantity of other medications being given to the patient that might interact with the compound, either potentiating it or inhibiting it, and other pharmacokinetic considerations such as liver and kidney function.

EXAMPLES

Example 1

Cyproheptadine was evaluated in three experiments: 1) as a countermeasure to sarin exposure, 2) as an antidote to sarin exposure, and 3) as an antidote to sarin exposure in combination with 2-PAM and diazepam. Initially, a dose response curve was determined using 1, 3, and 10 mg/kg cyproheptadine against a challenge of sarin (42 µg/ml) with the carboxyesterase inhibitor (CBDP). CBDP acts to prevent the excess carboxyesterase from scavenging sarin and therefore renders the nerve agent more potent. Table 1 shows that, in comparison to the vehicle alone treatment, cyproheptadine enhances survival from 58% to 100% at doses of 1, 3, or 10 mg/kg.

TABLE 1

Cyproheptadine after Exposure to Sarin (42 µg/ml) with CBDP

| Cyproheptadine Dose (mg/kg) | % Survival |
|---|---|
| 0 | 58 |
| 1 | 100 |
| 3 | 100 |
| 10 | 100 |

Table 2 shows data using cyproheptadine as an antidote after sarin (293 g/kg, ~LD50) exposure. In this model, modest improvement in survival was observed with cyproheptadine. The data show that, in comparison to the vehicle alone treatment, cyproheptadine enhances survival from 50% to 83% at doses of 1, 3, or 10 mg/kg.

TABLE 2

Cyproheptadine Can Promote Survival as an Antidote to Sarin Exposure.

| Cyproheptadine Dose (mg/kg) | % Survival |
|---|---|
| 0 | 50 |
| 0.3 | 67 |
| 1 | 83 |
| 3 | 83 |
| 10 | 83 |

Table 3 shows data obtained using cyproheptadine as a substitute for atropine. At 10 mg/kg, cyproheptadine was capable of promoting survival with an efficacy equivalent to that of atropine when combined with 2-PAM and diazepam following a challenge of $2.75 \times LD_{50}$ sarin.

TABLE 3

Cyproheptadine Shows Equivalent Survival Rates When Combined with 2-PAM/Diazepam in Comparison to Atropine/2-PAM/Diazepam Following Sarin Exposure.

| Antidote | Dose (mg/kg) | | | Cyproheptadine | % Survival |
|---|---|---|---|---|---|
| | Atropine | 2-PAM | Diazepam | | |
| Atropine, 2-PAM, diazepam | 10 | 25 | 1 | 0 | 75 |
| 2-PAM, diazepam | 0 | 25 | 1 | 0 | 0 |
| 2-PAM, diazepam, cyproheptadine | 0 | 25 | 1 | 1 | 0 |
| 2-PAM, diazepam, cyproheptadine | 0 | 25 | 1 | 3 | 0 |
| 2-PAM, diazepam, cyproheptadine | 0 | 25 | 1 | 10 | 67 |

Example 2

Further experiments were performed to compare atropine and cyproheptadine. As shown in Table 4 below, cyproheptadine was found to have a similar effective dose compared to atropine with respect to the treatment of sarin exposure as well as in a model of tremor model. Cyproheptadine and atropine were also found to have a toxicity (LD50) of greater than 30.0 mg/kg.

TABLE 4

| In vivo Experiment | Atropine (mg/kg) | Cyproheptadine (mg/kg) |
|---|---|---|
| Oxotremorine Induced Tremor Reduction | ED50: 1.08 | ED50: 0.96 |
| 2.75X Sarin Challenge | ED75: 10.0 mg/kg | ED67: 10.0 mg/kg |
| Toxicity: Lethal Dose | LD50: >30.0 mg/kg | LD50: >30 mg/kg. |

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure. All references, including patents, cited herein are incorporated by reference in their entirety.

What is claimed is:

1. A method of treating exposure to an organophosphate compound, comprising administering to a subject in need thereof a therapeutically effective amount of cyproheptadine and pharmaceutically acceptable salts, wherein the organophosphate compound is sarin thereof.

2. The method of claim 1, wherein the composition comprises a pharmaceutically acceptable excipient in combination with the compound.

3. The method of claim 1, wherein the therapeutically effective amount of the compound administered to the subject is between 0.1 and 10 mg/kg.

4. The method of claim 1, wherein the therapeutically effective amount of the compound administered to the subject is 3 mg/kg.

5. The method of claim 1, wherein the therapeutically effective amount of the compound is administered to the subject following exposure of the subject to the organophosphate compound.

6. The method of claim 1, wherein the therapeutically effective amount of the compound is administered to the subject prior to exposure of the subject to the organophosphate compound.

7. The method of claim 1, further comprising the step of administering atropine.

8. The method of claim 1, further comprising the step of administering pralidoxime (2-PAM).

9. The method of claim 1, further comprising the step of administering diazepam.

10. The method of claim 1, wherein the therapeutically effective amount of the compound administered to the subject is 1 mg/kg.

11. The method of claim 1, wherein the therapeutically effective amount of the compound administered to the subject is 10 mg/kg.

* * * * *